(12) United States Patent
Solazzi

(10) Patent No.: US 8,565,375 B2
(45) Date of Patent: Oct. 22, 2013

(54) PROTECTION DEVICE FOR X-RAY INSTRUMENTATION

(75) Inventor: Monte J. Solazzi, Palm City, FL (US)

(73) Assignee: Chemplex Industries, Inc., Palm City, FL (US)

( * ) Notice: Subject to any disclaimer, the term of this patent is extended or adjusted under 35 U.S.C. 154(b) by 370 days.

(21) Appl. No.: 13/066,393

(22) Filed: Apr. 14, 2011

(65) Prior Publication Data

US 2012/0263278 A1 Oct. 18, 2012

(51) Int. Cl.
*H05G 1/00* (2006.01)
*G21K 5/08* (2006.01)
*G01N 21/01* (2006.01)
*G01N 23/223* (2006.01)
*G01T 1/36* (2006.01)

(52) U.S. Cl.
USPC ........ 378/44; 378/208; 250/440.1; 250/491.1

(58) Field of Classification Search
USPC ................ 378/44–50, 204, 208, 210; 356/36, 356/300–305, 310, 440, 244, 246; 250/304, 250/440.11, 428, 432 R, 491.1, 526; 359/507, 510, 511; 73/52, 64, 56, 863, 73/864.81, 864.83, 864.91, 431; 206/730–735, 305, 460, 775–778

See application file for complete search history.

(56) References Cited

U.S. PATENT DOCUMENTS

| | | |
|---|---|---|
| D238,693 S | 2/1976 | Solazzi |
| 4,409,854 A | 10/1983 | Solazzi |
| 4,643,033 A | 2/1987 | Solazzi |
| 4,665,759 A | 5/1987 | Solazzi |
| 4,698,210 A | 10/1987 | Solazzi |
| 5,451,375 A | 9/1995 | Solazzi |
| 5,454,020 A | 9/1995 | Solazzi |
| 5,630,989 A | 5/1997 | Solazzi |
| 5,958,345 A * | 9/1999 | Turner et al. ................. 422/561 |
| 6,009,766 A | 1/2000 | Solazzi |
| 6,428,751 B1 | 8/2002 | Solazzi |
| 7,722,821 B2 | 5/2010 | Solazzi |
| 7,981,380 B2 | 7/2011 | Solazzi |
| 2004/0208792 A1 * | 10/2004 | Linton et al. ................... 422/99 |

* cited by examiner

*Primary Examiner* — Anastasia Midkiff
(74) *Attorney, Agent, or Firm* — Keene IP Law, LLC

(57) ABSTRACT

An accessory, method, and system is provided for protecting the lower chamber of X-ray spectroscopic instrumentation during analysis, the instrumentation including an upper chamber, a lower chamber, and a dividing plate, the lower chamber including an X-ray detector and an excitation source, the accessory including: a frame with a centrally-located aperture extending from one side of the frame to an opposite side of the frame; an adhesive layer disposed on each side of the frame; a thin film of polymeric material disposed on one side of the frame; and a removably attached release sheet on the adhesive layer disposed on the opposite side of the frame, where the accessory is disposed on a surface of the dividing plate to protect the lower chamber of the instrumentation from damage.

20 Claims, 2 Drawing Sheets

PROTECTION DEVICE FOR X-RAY INSTRUMENTATION

FIELD OF THE INVENTION

The invention relates generally to protection devices for protecting X-ray instrumentation, and more particularly, to protection devices that protect the lower electronics portion of an X-ray instrument.

BACKGROUND OF THE INVENTION

Sample cups are used with X-ray spectroscopic instrumentation to determine the characteristics or properties of various substances contained in the cups. The sample substances are disposed in a central chamber of a sample cup for analysis. The sample cup may include a thin film of material disposed across one end of the cup to retain the sample. The sample substance contained in the cup is subjected to analysis when X-ray beams impinge upon the thin film.

During analysis, the sample substance contained in a sample cup may escape or exude from the central chamber of the sample cup and into the X-ray analysis chamber, or onto an X-ray tube, an X-ray detector, and other electronics contained in the lower chamber of the X-ray instrument, causing damage to the X-ray tube and associated X-ray windows, X-ray detectors, and the electronics. In addition, the exuded sample substance may also cause contamination issues, costly cleanups, and non-productive down time.

There remains a need for a protection device for X-ray instrumentation that substantially eliminates the possibility of damage and contamination.

SUMMARY OF THE INVENTION

According to an aspect of the invention, an accessory for protecting the lower chamber of X-ray spectroscopic instrumentation during analysis is described, where the X-ray spectroscopic instrumentation includes an upper chamber, a lower chamber, and a dividing plate separating the chambers, and the lower chamber includes an X-ray detector and an excitation source, the accessory including: a frame with a centrally-located aperture extending from one side of the frame to an opposite side of the frame; an adhesive layer disposed on each side of the frame; a thin film of polymeric material disposed on one side of the frame; and a removably attached release sheet on the adhesive layer disposed on the opposite side of the frame, wherein the accessory is disposed on a surface of the dividing plate to protect the lower chamber of the instrumentation from damage.

According to an aspect of the invention, a method for protecting spectroscopic instrumentation during analysis is described, and includes the steps of: providing a frame with a centrally-located aperture extending from one side of the frame to an opposite side of the frame; providing an adhesive layer on each side of the frame; providing a thin film of polymeric material; affixing the thin film of polymeric material on one side of the frame with the adhesive layer, the thin film of polymeric material covering the centrally-located aperture; providing an X-ray spectroscopic instrumentation device having an upper chamber and a lower chamber, each chamber being separated by a dividing plate having an aperture through which radiation is emitted and detected; and affixing the opposite side of the frame with the adhesive layer onto a surface of the dividing plate, wherein the thin film of polymeric material covers the aperture of the dividing plate.

According to another aspect of the invention, a system for protecting instrumentation used in spectroscopic analysis, including: a cell body configured for receiving a sample substance; a frame with a centrally-located aperture extending from one side of the frame to an opposite side of the frame, the frame including an adhesive layer on each side thereof; a thin film of polymeric material disposed on one side of the frame by the adhesive layer, the thin film of polymeric material covering the centrally-located aperture; an X-ray spectroscopic instrumentation device having an upper chamber and a lower chamber, each chamber being separated by a dividing plate having an aperture through which radiation is emitted and detected; and an opposite side of the frame disposed onto a surface of the dividing plate and across the aperture of the dividing plate, the opposite side of the frame affixed to a surface of the dividing plate by the adhesive layer, wherein a sample substance disposed in the cell body and undergoing analysis is retained by the thin film and the lower chamber is protected from the sample substance is described.

BRIEF DESCRIPTION OF THE DRAWINGS

Throughout the drawings, like reference numerals are used to indicate common features of the described devices.

The above-identified drawing figures set forth several of the preferred embodiments of the invention. Other embodiments are also contemplated, as disclosed herein. The disclosure represents the invention, but is not limited thereby, as it should be understood that numerous other modifications and embodiments may be devised by those skilled in the art which fall within the scope and spirit of the invention as claimed.

DETAILED DESCRIPTION OF THE INVENTION

As used herein, the terms "comprises", "comprising", "includes", "including", "has", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "of" refers to an inclusive "or" and not to an exclusive "or". For example, a condition A or B is satisfied by any one of the following: A is true (or present) and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description herein should be read and understood to include one or at least one. In addition, the singular also includes the plural unless indicated to the contrary. For example, reference to a composition containing "a compound" includes one or more compounds. As used in this specification and the appended claims, the term "or" is generally employed in its sense including "and/or" unless the content clearly dictates otherwise.

All numeric values are herein assumed to be modified by the term "about," whether or not explicitly indicated. The term "about" generally refers to a range of numbers that one of skill in the art would consider equivalent to the recited value (i.e., having the same function or result). In any instances, the terms "about" may include numbers that are rounded to the nearest significant figure.

Figure 1:
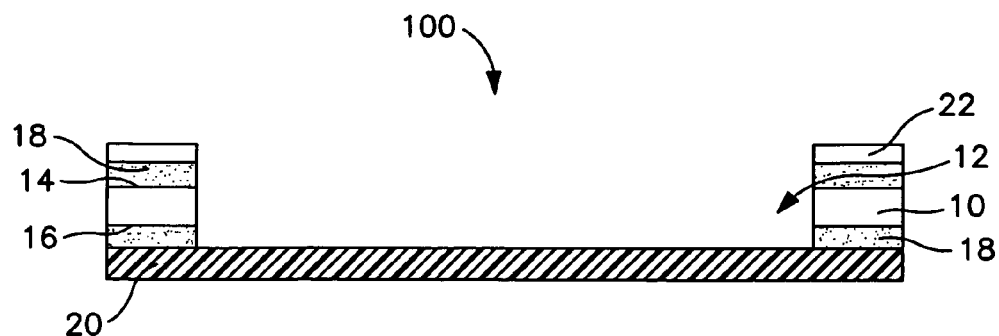
FIG. 1 is a cross-sectional view illustrating the protection device according to an aspect of the invention.
Figure 2:
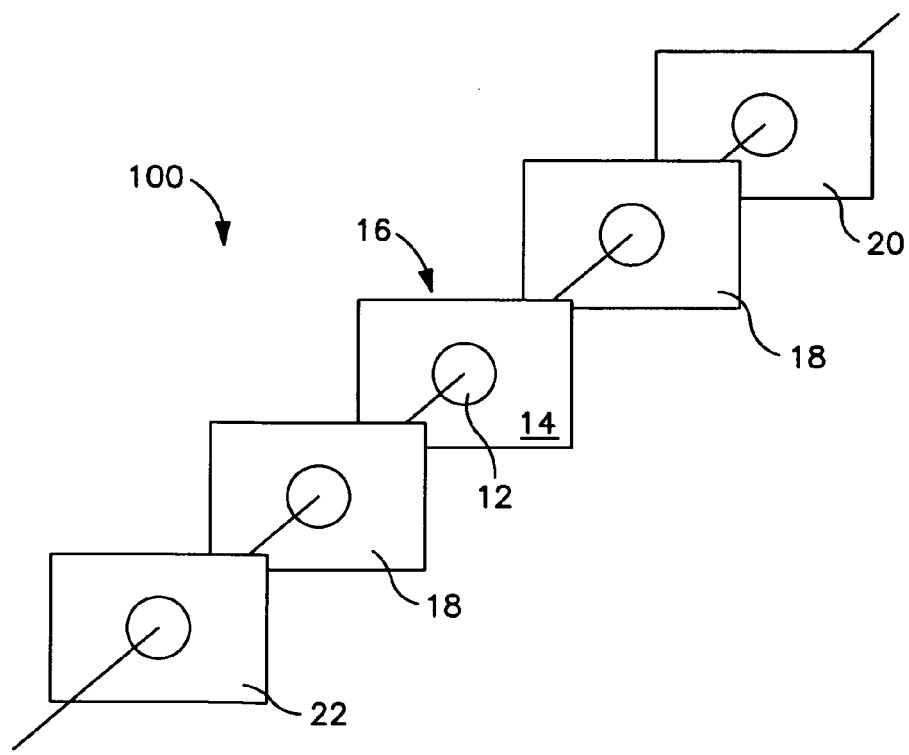
FIG. 2 is an exploded perspective view illustrating the protection device of FIG. 1 according to an aspect of the invention.

Referring to FIG. 1, according to an aspect of the invention, a protection device 100 includes a frame 10 with a centrally-located aperture 12. The aperture 12 extends from one side 14 of the frame 10 to the opposite side 16 thereof. Although illustrated as a circular aperture, it should be understood that other geometrics may be employed, for example, the aperture may be square or rectangular, provided the aperture is of sufficient size to permit X-ray beams from a lower chamber of X-ray instrumentation to impinge upon a sample undergoing analysis.

Still referring to FIG. 1, an adhesive layer 18 is disposed on each side of the frame 10. In one aspect, the adhesive layer 18 is a cold temperature adhesive. Suitable adhesives for use are available from Kenco of Milwaukee, Wis. On the adhesive layer 18 on one side of the frame 10, a thin film of polymeric material 20 is disposed. On the adhesive layer on the opposite side of the frame 10, a removably attached release sheet 22 is disposed.

The frame 10 may be formed of paper, plastic, or label stock, and should be compatible with the adhesive applied thereon. The frame 10 may be flexible or rigid. The thin film of polymeric material 20 may be formed from polyethylene, polyester, polyethylene terephthalate, polypropylene, polyimide, polycarbonate, ETNOM, or other materials exhibiting minimal and comparative absorption that are suitable for spectroscopic analysis. The ETNOM brand of thin film material is available from Chemplex Industries, Inc.

The frame 10 may have dimensions of about 4 inches by 4 inches (101.6 mm), and a thickness of about 0.5 mm. The aperture 12 may have a diameter of about 3¼ inches (82.6 mm). It should be understood that other geometrics may be employed, and the dimensions of the frame 10 and the aperture 12 described herein should not be limited thereby.

Figure 3:
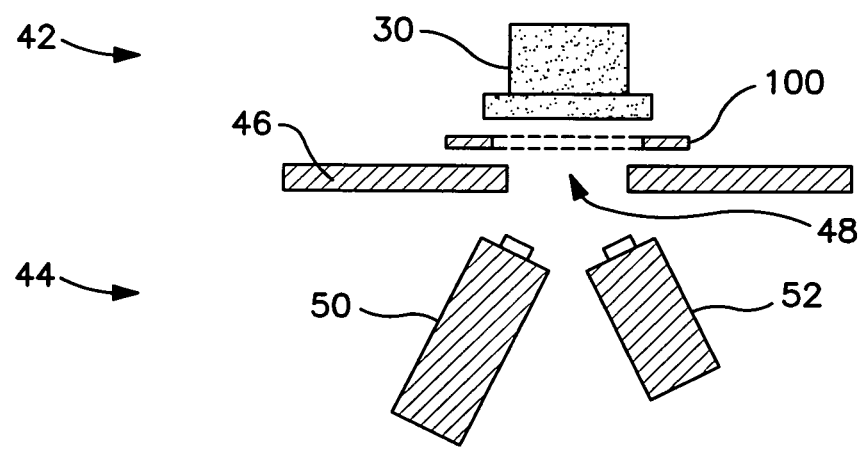
FIG. 3 is a view of the system illustrating the protection device of FIG. 1 in context according to an aspect of the invention.

Referring to FIG. 3, the system according to an aspect of the invention is illustrated. In FIG. 3, a sample cup 30 is illustrated in the upper chamber 42 of the X-ray instrument. In the lower chamber 44, an excitation source 50 and X-ray detector 52 are illustrated. The protection device 100 is illustrated in context above a platform, herein referred to as a dividing plate 46 with an aperture 48. In this aspect, an analyst would assemble a sample cup 30 and dispose an analyte into the central chamber of the cup 30. Prior to analysis, a protection device 100 is placed on the dividing plate 46 of the X-ray instrument by removing the release sheet 22 to expose the adhesive layer 18. The device 100 is centered around the aperture 48 of the dividing plate 46, and the exposed adhesive is disposed on an upper surface of the plate 46. In one aspect of the invention, the adhesive is pressure-sensitive. To ensure an effective seal, the device 100 may be pressed against the upper surface of the dividing plate 46.

Upon placement of the device 100 on the dividing plate 46, the prepared sample cup is placed in the upper chamber 42 for analysis. The aperture 48 in the dividing plate 46 allows the X-rays emitted from the X-ray tube 50 in the lower chamber 44 to strike the sample plane (defined as the thin-film sample support retaining the sample substance in the sample cup in the upper chamber). In response to irradiation, the sample substance emits a characteristic radiation that is directed to travel through the same aperture 48 in the dividing plate 46. The X-ray detector 52 receives the signals and electronically sorts them in accordance with the elemental spectral line for element identification, and energy of the spectral line indicative of the quantity of the elements, for example, percent concentration, parts per million, and parts per billion. The X-ray tube has a very thin window for accepting the radiation and to minimize the absorption of the emitted X-rays and the characteristic radiation of the excited sample.

Advantageously, by using a protection device 100 as described herein, a user can place prepared sample cups in the X-ray instrument for analysis, and when the sample undergoing analysis escapes or exudes from the sample cup, the sensitive electronics, including X-ray tube windows and X-ray detectors, are protected from damage. As an additional advantage, by protecting the electronics of the instrument, contamination is unlikely, and there are fewer clean-ups and less non-productive down time. Furthermore, the protection device 100 may be removed and easily replaced with an unused device 100, particularly when the thin film of material 20 becomes brittle after extended use.

The invention has been described with reference to specific embodiments. One of ordinary skill in the art, however, appreciates that various modifications and changes can be made without departing from the scope of the invention as set forth in the claims. For example, although the frame may be substantially square according to an aspect of the invention, the frame may take many forms, dependent upon the shape of the analysis chamber and the diameter of the aperture of the dividing plate in the X-ray instrumentation. Accordingly, the specification is to be regarded in an illustrative manner, rather than with a restrictive view, and all such modifications are intended to be included within the scope of the invention.

Benefits, other advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

What is claimed is:

1. An accessory for protecting the lower chamber of X-ray spectroscopic instrumentation during analysis, said X-ray spectroscopic instrumentation including an upper chamber, a lower chamber, and a dividing plate separating said chambers, said lower chamber including an X-ray detector and an excitation source, said accessory comprising:
    a frame with a centrally-located aperture extending from one side of said frame to an opposite side of said frame;
    an adhesive layer disposed on each side of said frame;
    a thin film of polymeric material disposed on one side of said frame; and
    a removably attached release sheet on said adhesive layer disposed on said opposite side of said frame,
    wherein said accessory is disposed on a surface of said dividing plate to protect said lower chamber of said instrumentation from damage.

2. The accessory according to claim 1, wherein said frame is formed of paper.

3. The accessory according to claim 1, wherein said frame is formed of plastic.

4. The accessory according to claim 1, wherein said frame is formed of label stock.

5. The accessory according to claim 1, wherein said thin film of polymeric material is formed of polyethylene.

6. The accessory according to claim 1, wherein said thin film of polymeric material is formed of polyester.

7. The accessory according to claim 1, wherein said thin film of polymeric material is formed of polyethylene terephthalate.

8. The accessory according to claim 1, wherein said thin film of polymeric material is formed of polypropylene.

9. The accessory according to claim 1, wherein said thin film of polymeric material is formed of polyimide.

10. The accessory according to claim 1, wherein said thin film of polymeric material is formed of polycarbonate.

11. The accessory according to claim 1, wherein said thin film of polymeric material is formed of ETNOM.

12. The accessory according to claim 1, wherein said adhesive layer is formed of a cold-temperature adhesive.

13. The accessory according to claim 1, wherein said adhesive layer is pressure-sensitive.

14. A method for protecting spectroscopic instrumentation during analysis, comprising the steps of:
   providing a frame with a centrally-located aperture extending from one side of said frame to an opposite side of said frame;
   providing an adhesive layer on each side of said frame;
   providing a thin film of polymeric material;
   affixing said thin film of polymeric material on one side of said frame with said adhesive layer, said thin film of polymeric material covering said centrally-located aperture;
   providing an X-ray spectroscopic instrumentation device having an upper chamber and a lower chamber, each chamber being separated by a dividing plate having an aperture through which radiation is emitted and detected; and
   affixing said opposite side of said frame with said adhesive layer onto a surface of said dividing plate,
   wherein said thin film of polymeric material covers said aperture of said dividing plate.

15. The method according to claim 14, further comprising the steps of:
   providing a cell body configured for receiving a sample substance;
   disposing a sample substance into said cell body; and
   subjecting the sample substance to analysis,
   wherein said sample substance undergoing analysis is retained by said thin film and said lower chamber is protected from said sample substance.

16. The method according to claim 14, further comprising the step of:
   providing a removably attached release sheet on said adhesive layer disposed on said opposite side of said frame.

17. The method according to claim 14, wherein said lower chamber of said instrumentation device includes an X-ray detector and an excitation source.

18. A system for protecting instrumentation used in spectroscopic analysis, comprising:
   a cell body configured for receiving a sample substance;
   a frame with a centrally-located aperture extending from one side of said frame to an opposite side of said frame, said frame including an adhesive layer on each side thereof;
   a thin film of polymeric material disposed on one side of said frame by said adhesive layer, said thin film of polymeric material covering said centrally-located aperture;
   an X-ray spectroscopic instrumentation device having an upper chamber and a lower chamber, each chamber being separated by a dividing plate having an aperture through which radiation is emitted and detected; and
   an opposite side of said frame disposed onto a surface of said dividing plate and across said aperture of said dividing plate, said opposite side of said frame affixed to a surface of said dividing plate by said adhesive layer,
   wherein a sample substance disposed in said cell body and undergoing analysis is retained by said thin film and said lower chamber is protected from said sample substance.

19. The system according to claim 18, further comprising:
   a removably attached release sheet disposed on said adhesive layer on said opposite side of said frame.

20. The system according to claim 18, wherein said lower chamber of said instrumentation device includes an X-ray detector and an excitation source.

* * * * *